(12) United States Patent
Kamiguchi

(10) Patent No.: US 12,145,005 B2
(45) Date of Patent: Nov. 19, 2024

(54) PARTICLE BEAM TREATMENT APPARATUS AND ACCELERATOR

(71) Applicant: SUMITOMO HEAVY INDUSTRIES, LTD., Tokyo (JP)

(72) Inventor: Nagaaki Kamiguchi, Kanagawa (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 272 days.

(21) Appl. No.: 17/706,214

(22) Filed: Mar. 28, 2022

(65) Prior Publication Data
US 2022/0305295 A1 Sep. 29, 2022

(30) Foreign Application Priority Data
Mar. 29, 2021 (JP) ................................. 2021-055419

(51) Int. Cl.
*A61N 5/10* (2006.01)
*H05H 7/08* (2006.01)

(52) U.S. Cl.
CPC ......... *A61N 5/1065* (2013.01); *A61N 5/1043* (2013.01); *A61N 5/1077* (2013.01); *H05H 7/08* (2013.01); *A61N 2005/1087* (2013.01); *H05H 2007/081* (2013.01)

(58) Field of Classification Search
None
See application file for complete search history.

(56) References Cited

U.S. PATENT DOCUMENTS

| 6,265,837 | B1 * | 7/2001 | Akiyama | A61N 5/1043 |
| | | | | 315/501 |
| 2010/0243911 | A1 * | 9/2010 | Fujii | A61N 5/1044 |
| | | | | 250/400 |
| 2017/0165504 | A1 * | 6/2017 | Dollinger | A61N 5/1048 |
| 2019/0299029 | A1 * | 10/2019 | Inoue | A61N 5/1081 |

FOREIGN PATENT DOCUMENTS

JP 2017-209372 A 11/2017

\* cited by examiner

*Primary Examiner* — Eliza W Osenbaugh-Stewart
(74) *Attorney, Agent, or Firm* — Michael Best & Friedrich LLP (57) ABSTRACT

Provided is a particle beam treatment apparatus irradiating an irradiation target with a particle beam. The apparatus includes: an accelerator that generates the particle beam in an acceleration space; and an irradiation unit that virtually divides the irradiation target into a plurality of layers and irradiates each layer while performing scanning with the particle beam with a scanning electromagnet. The accelerator includes a particle generation unit generating particles that are to accelerate in the acceleration space, and the accelerator sets a parameter of the particle generation unit based on at least one of the layers of the irradiation target and adjusts an intensity of the particle beam based on the set parameter.

14 Claims, 9 Drawing Sheets

PARTICLE BEAM TREATMENT APPARATUS AND ACCELERATOR

RELATED APPLICATIONS

The content of Japanese Patent Application No. 2021-055419, on the basis of which priority benefits are claimed in an accompanying application data sheet, is in its entirety incorporated herein by reference.

BACKGROUND

Technical Field

Certain embodiments of the present invention relates to a particle beam treatment apparatus and an accelerator.

Description of Related Art

In the related art, for example, an apparatus is known as a particle beam treatment apparatus performing treatment by irradiating a patient's affected part with a particle beam. In the particle beam treatment apparatus described in the related art, an irradiation unit performs the irradiation with the particle beam by a scanning method. In other words, the irradiation unit performs irradiation while moving the position of particle beam irradiation with respect to the affected part by scanning with a scanning electromagnet.

SUMMARY

A particle beam treatment apparatus according to one aspect of the present invention is a particle beam treatment apparatus irradiating an irradiation target with a particle beam. The apparatus includes: an accelerator that generates the particle beam in an acceleration space; and an irradiation unit that virtually divides the irradiation target into a plurality of layers and irradiates each layer while performing scanning with the particle beam with a scanning electromagnet. The accelerator includes a particle generation unit generating particles that are to accelerate in the acceleration space, and the accelerator sets a parameter of the particle generation unit based on at least one of the layers of the irradiation target and adjusts an intensity of the particle beam based on the set parameter.

The accelerator sets the parameter of the particle generation unit based on at least one layer of the irradiation target and adjusts the intensity of the particle beam based on the set parameter. In a case where the maximum intensity of the particle beam required in the layer to be irradiated is low in this case, the particle generation unit is capable of generating particles in a state of being suppressed to a parameter capable of corresponding to a low intensity. As a result, the parameter at the particle beam generation unit can be suppressed to an appropriate size. In addition, the accelerator adjusts the intensity of the particle beam such that an energy corresponding to the irradiation position of the particle beam can be obtained, and thus a desired dose can be obtained by short-time irradiation even without irradiating the irradiation position for a long time. From the above, it is possible to increase the scanning speed of the particle beam while adjusting the intensity of the particle beam in an appropriate adjustment mode.

The accelerator may set the parameter of the particle generation unit based on the maximum intensity for at least one layer. An adjusting unit adjusts the intensity by scraping a part of the particle beam with a damper, and thus it is impossible to perform the adjustment for an increase in intensity. Accordingly, it is possible to suppress an insufficient intensity of the output particle beam by setting the parameter of the particle beam generation unit based on the maximum intensity with respect to the layer.

The accelerator may set the parameter of the particle generation unit so as to obtain an output in which a predetermined intensity is increased with respect to the maximum intensity. In this case, it is possible to suppress an insufficient intensity by setting a parameter capable of outputting a large intensity in advance even in a case where the particle beam intensity is lower than planned even at the same parameter due to a change over time at the particle generation unit.

In the particle beam treatment apparatus, the accelerator includes an adjusting unit adjusting the intensity of the particle beam by bending the particle beam with a deflector and scraping a part of the particle beam with a damper in the acceleration space. Accordingly, the adjusting unit adjusts the amount of scraping such that the intensity corresponding to the irradiation position of the particle beam can be obtained and thus is capable of obtaining a desired dose by short-time irradiation even without irradiating the irradiation position for a long time.

The accelerator may adjust the intensity of the particle beam based on a data table prepared in advance. In this case, the accelerator is capable of appropriately adjusting the intensity of the particle beam with the load of calculation reduced.

The irradiation unit may have a detection unit detecting the intensity of the particle beam, and the accelerator may feed back a detection result of the detection unit to adjust the intensity of the particle beam. In this case, the intensity of the particle beam can be appropriately controlled based on the detection result at the detection unit even in a case where the intensity of the particle beam is different from a planned one.

An accelerator according to one aspect of the present invention is an accelerator that virtually divides an irradiation target into a plurality of layers and generates a particle beam for irradiating each layer by a scanning method. The accelerator includes a particle generation unit generating particles in an acceleration space. A parameter of the particle generation unit based on at least one of the layers of the irradiation target is set and an intensity of the particle beam is adjusted based on the set parameter.

DETAILED DESCRIPTION

In a case where the irradiation unit performs the irradiation with the particle beam by the scanning method, the irradiation unit responds by lengthening the irradiation time for each irradiation position in order to increase the dose with respect to the position. In order for the irradiation unit to irradiate at a high scanning speed and shorten the treatment time, an ion source parameter may be set to the maximum and the intensity of the particle beam may be adjusted by scraping a part of the particle beam with a damper. However, such a method may cause the parameter of the particle generation unit to become equal to or higher than necessary, which may lead to a decrease in the service life of the particle generation unit. Accordingly, it is required to adjust the intensity of a particle beam in an appropriate manner.

The present invention is to provide a particle beam treatment apparatus and an accelerator capable of increasing the scanning speed of a particle beam while adjusting the intensity of the particle beam in an appropriate adjustment mode.

According to this accelerator, it is possible to obtain the same action and effect as the particle beam treatment apparatus described above.

According to the present invention, it is possible to provide a particle beam treatment apparatus and an accelerator capable of increasing the scanning speed of a particle beam while adjusting the intensity of the particle beam in an appropriate adjustment mode.

Hereinafter, a particle beam treatment apparatus according to one embodiment of the present invention will be described with reference to the accompanying drawings. In the description of the drawings, the same elements are denoted by the same reference numerals with redundant description omitted.

Figure 1:
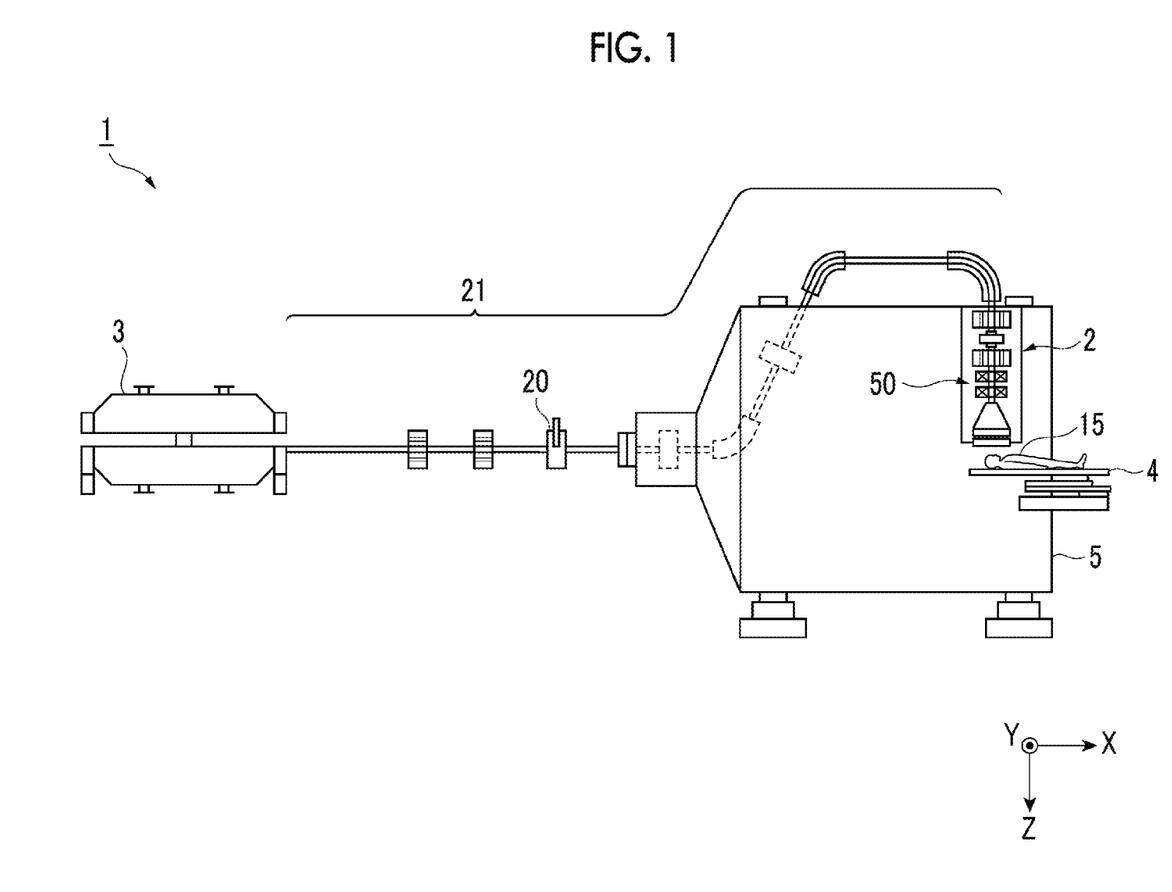
FIG. 1 is a schematic configuration diagram illustrating a particle beam treatment apparatus according to an embodiment of the present invention.

FIG. 1 is a schematic configuration diagram illustrating a particle beam treatment apparatus 1 according to one embodiment of the present invention. The particle beam treatment apparatus 1 is a system used for radiation therapy-based cancer treatment or the like. The particle beam treatment apparatus 1 includes an accelerator 3 that accelerates charged particles generated by an ion source device and emits the particles as a particle beam, an irradiation unit 2 that irradiates an irradiation target with the particle beam, and a beam transport line 21 that transports the particle beam emitted from the accelerator 3 to the irradiation unit 2. The irradiation unit 2 is attached to a rotating gantry 5 provided so as to surround a treatment table 4. The irradiation unit 2 can be rotated around the treatment table 4 by the rotating gantry 5. More detailed configurations of the accelerator 3, the irradiation unit 2, and the beam transport line 21 will be described later.

Figure 2:
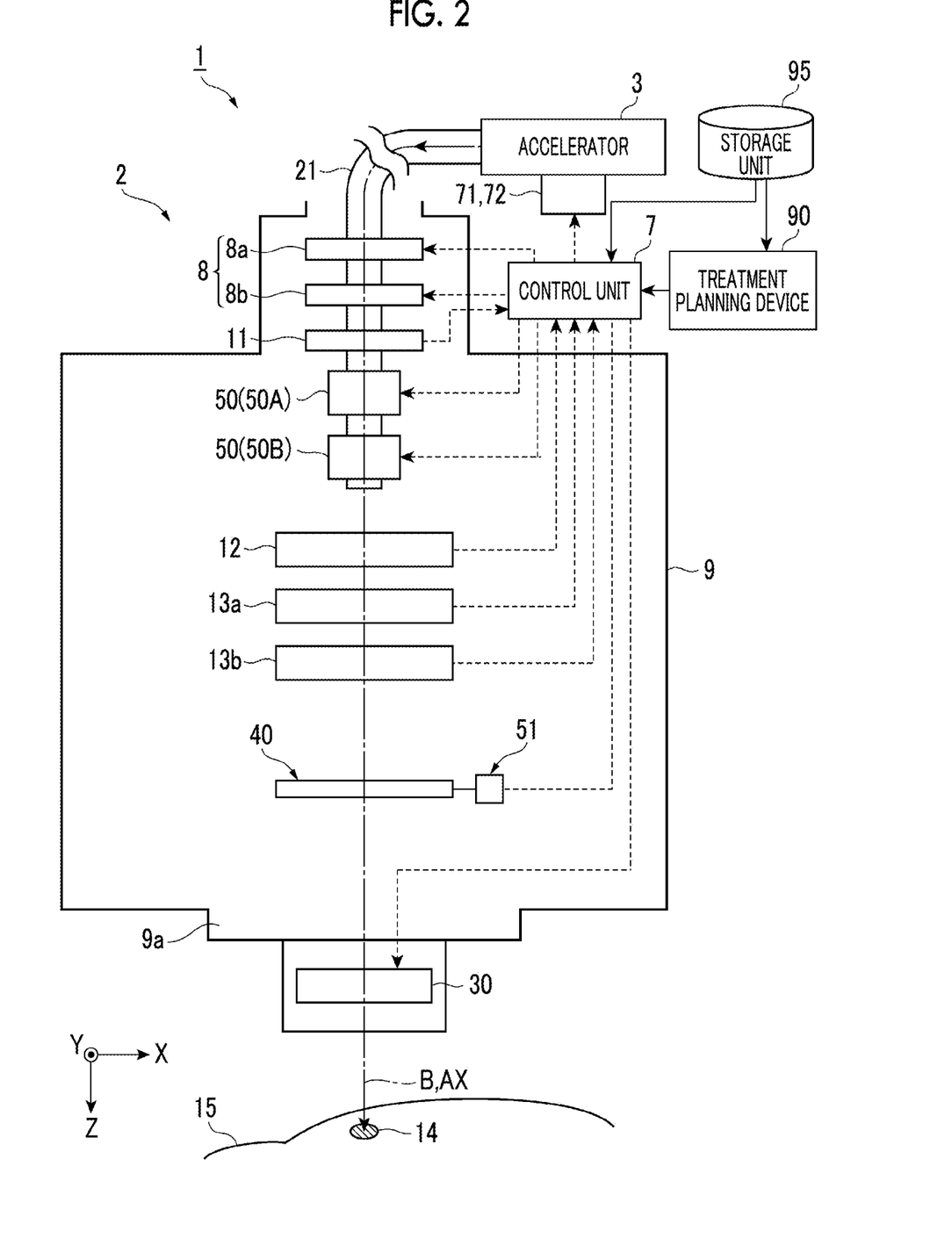
FIG. 2 is a schematic configuration diagram of the vicinity of an irradiation unit of a particle beam treatment apparatus of FIG. 1.

FIG. 2 is a schematic configuration diagram of the vicinity of the irradiation unit of the particle beam treatment apparatus 1 of FIG. 1. "X-axis direction", "Y-axis direction", and "Z-axis direction" will be used in the following description. "Z-axis direction" is the direction in which a base axis AX of a particle beam B extends and is the depth direction of irradiation with the particle beam B. "Base axis AX" is the irradiation axis of the particle beam B that is not deflected by scanning electromagnets 50 (described later). FIG. 2 illustrates how irradiation with the particle beam B is performed along the base axis AX. "X-axis direction" is one direction in a plane perpendicular to the Z-axis direction. "Y-axis direction" is perpendicular to the X-axis direction in the plane perpendicular to the Z-axis direction.

First, a schematic configuration of the particle beam treatment apparatus 1 according to the present embodiment will be described with reference to FIG. 2. The particle beam treatment apparatus 1 is a scanning method-related irradiation apparatus. The scanning method is not particularly limited, and line scanning, raster scanning, spot scanning, and so on may be adopted. As illustrated in FIG. 2, the particle beam treatment apparatus 1 includes the accelerator 3, the irradiation unit 2, the beam transport line 21, a control unit 7, a treatment planning device 90, and a storage unit 95.

The accelerator 3 is a device that accelerates charged particles and emits the particle beam B of preset intensity. Examples of the accelerator 3 include a cyclotron and a synchrocyclotron. In a case where a cyclotron that emits the particle beam B of predetermined intensity is adopted as the accelerator 3, it is possible to adjust (decrease) the energy of the particle beam sent to the irradiation unit 2 by adopting an energy adjustment unit 20 (see FIG. 1). The accelerator 3 is connected to the control unit 7, and a supplied current is controlled. The particle beam B generated by the accelerator 3 is transported to the irradiation unit 2 by the beam transport line 21. The beam transport line 21 connects the accelerator 3, the energy adjustment unit 20, and the irradiation unit 2 and transports the particle beam emitted from the accelerator 3 to the irradiation unit 2.

The irradiation unit 2 irradiates a tumor (irradiation target) 14 in the body of a patient 15 with the particle beam B. The particle beam B is charged particles accelerated to a high speed, and examples thereof include a proton beam, a heavy particle (heavy ion) beam, and a electron beam. Specifically, the irradiation unit 2 is a device that irradiates the tumor 14 with the particle beam B emitted from the accelerator 3 accelerating the charged particles generated by the ion source (not illustrated) and transported by the beam transport line 21. The irradiation unit 2 includes the scanning electromagnets 50, a quadrupole electromagnet 8, a profile monitor 11, a dose monitor 12, position monitors 13a and 13b, a collimator 40, and a degrader 30. The scanning electromagnets 50, the monitors 11, 12, 13a, and 13b, the quadrupole electromagnet 8, and the degrader 30 are accommodated in an irradiation nozzle 9 as an accommodating body. The irradiation unit 2 is configured by the irradiation nozzle 9 accommodating the main components as described above. The quadrupole electromagnet 8, the profile monitor 11, the dose monitor 12, the position monitors 13a and 13b, and the degrader 30 may be omitted.

An X-axis direction scanning electromagnet 50A and a Y-axis direction scanning electromagnet 50B are used as the scanning electromagnets 50. Each of the X-axis direction scanning electromagnet 50A and the Y-axis direction scanning electromagnet 50B is configured by a pair of electromagnets. The magnetic field between the pair of electromagnets is changed in accordance with the current supplied from the control unit 7, and scanning is performed with the particle beam B passing between the electromagnets. The X-axis direction scanning electromagnet 50A performs scanning with the particle beam B in the X-axis direction, and the Y-axis direction scanning electromagnet 50B performs scanning with the particle beam B in the Y-axis direction. The scanning electromagnets 50 are disposed in this order on the base axis AX downstream of the accelerator 3 in the advancing direction of the particle beam B. The scanning electromagnet 50 performs scanning with the particle beam B such that irradiation with the particle beam B is performed in a scan pattern pre-planned by the treatment planning device 90. How to control the scanning electromagnet 50 will be described later.

The quadrupole electromagnet 8 includes an X-axis direction quadrupole electromagnet 8a and a Y-axis direction quadrupole electromagnet 8b. The X-axis direction quadrupole electromagnet 8a and the Y-axis direction quadrupole electromagnet 8b throttle and converge the particle beam B in accordance with the current supplied from the control unit 7. The X-axis direction quadrupole electromagnet 8a converges the particle beam B in the X-axis direction, and the Y-axis direction quadrupole electromagnet 8b converges the particle beam B in the Y-axis direction. It is possible to change the beam size of the particle beam B by changing the throttle amount (convergence amount) by changing the current supplied to the quadrupole electromagnet 8. The quadrupole electromagnet 8 is disposed in this order on the base axis AX between the accelerator 3 and the scanning electromagnet 50. The beam size is the size of the particle beam B in the XY plane. The shape of the beam is the shape of the particle beam B in the XY plane.

The profile monitor 11 detects the beam shape and the position of the particle beam B for alignment at initial setting. The profile monitor 11 is disposed between the quadrupole electromagnet 8 and the scanning electromagnet 50 on the base axis AX. The dose monitor 12 detects the dose of the particle beam B. The dose monitor 12 is disposed downstream of the scanning electromagnet 50 on the base axis AX. The position monitors 13a and 13b detect and monitor the beam shape and the position of the particle beam B. The position monitors 13a and 13b are disposed on the base axis AX downstream of the dose monitor 12 in the advancing direction of the particle beam B. The monitors 11, 12, 13a, and 13b output detection results to the control unit 7.

The degrader 30 reduces the intensity of the particle beam B that passes to finely adjust the intensity of the particle beam B. In the present embodiment, the degrader 30 is provided on a tip portion 9a of the irradiation nozzle 9. The tip portion 9a of the irradiation nozzle 9 is an end portion on the downstream side of the particle beam B.

The collimator 40 is provided at least downstream of the scanning electromagnet 50 in the advancing direction of the particle beam B. The collimator 40 is a member that blocks the particle beam B in part and allows the particle beam B to pass in part. Here, the collimator 40 is provided downstream of the position monitors 13a and 13b. The collimator 40 is connected to a collimator drive unit 51, which moves the collimator 40.

The control unit 7 is configured by, for example, a CPU, a ROM, a RAM, and so on. The control unit 7 controls the accelerator 3, the scanning electromagnet 50, the quadrupole electromagnet 8, and the collimator drive unit 51 based on detection results output from the monitors 11, 12, 13a, and 13b.

In addition, the control unit 7 of the particle beam treatment apparatus 1 is connected to the treatment planning device 90 performing particle beam treatment planning and the storage unit 95 storing various data. The treatment planning device 90 measures the tumor 14 of the patient 15 by CT or the like before treatment and plans a radiation dose distribution at each position of the tumor 14 (radiation dose distribution of particle beams to be emitted). Specifically, the treatment planning device 90 creates a scan pattern with respect to the tumor 14. The treatment planning device 90 transmits the created scan pattern to the control unit 7. Planned in the scan pattern created by the treatment planning device 90 are a scanning path to be drawn by the particle beam B and the scanning speed at which the drawing is to be performed.

In a case where irradiation with the particle beam is performed by a scanning method, the tumor 14 is virtually divided into a plurality of layers in the Z-axis direction and scanning and irradiation with the particle beam are performed in one layer so as to follow the scanning path determined in the treatment planning. After the irradiation in the layer is completed, irradiation with the particle beam B is performed in the adjacent next layer.

In a case where irradiation with the particle beam B is performed by a scanning method and the particle beam treatment apparatus 1 illustrated in FIG. 2, the quadrupole electromagnet 8 is operated (ON) such that the passing particle beam B converges.

Subsequently, the particle beam B is emitted from the accelerator 3. Scanning with the emitted particle beam B is performed under the control of the scanning electromagnet 50 so as to follow the scan pattern determined in the treatment planning. As a result, the tumor 14 is irradiated with the particle beam B while being scanned within the irradiation range in one layer set in the Z-axis direction. The next layer is irradiated with the particle beam B after the irradiation in one layer is completed.

Figure 3A:
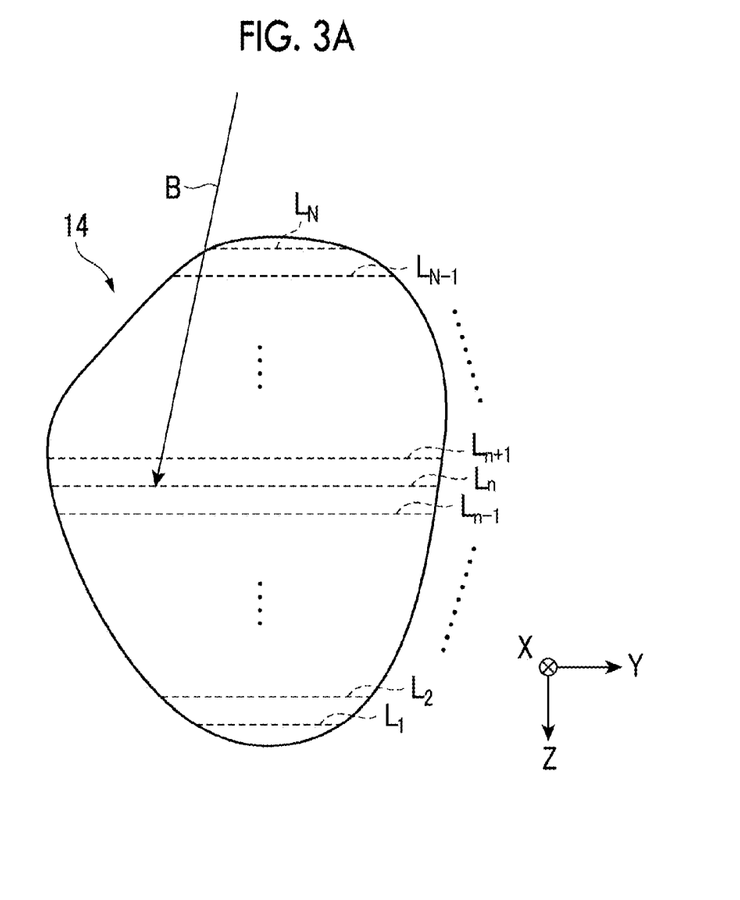
FIGS. 3A and 3B are diagrams illustrating layers set with respect to a tumor.
Figure 3B:
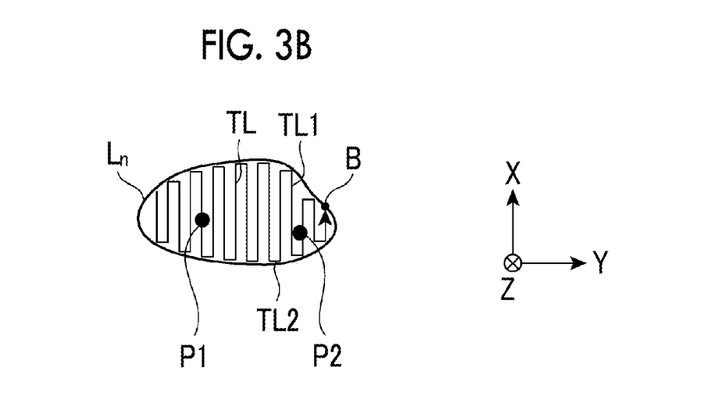

The particle beam irradiation image of the scanning electromagnet 50 controlled by the control unit 7 will be described with reference to FIGS. 3A and 3B. FIG. 3A illustrates an irradiation target virtually sliced into a plurality of layers in the depth direction. FIG. 3B illustrates a particle beam scanning image in one layer viewed from the depth direction.

As illustrated in FIG. 3A, the irradiation target is virtually sliced into a plurality of layers in the depth direction of irradiation and, in this example, is virtually sliced into the N layers of a layer L1, a layer L2, . . . a layer Ln−1, a layer Ln, a layer Ln+1, . . . a layer LN−1, and a layer LN in order from the deep layer (with a long range of the particle beam B). In addition, as illustrated in FIG. 3B, the particle beam B is, while drawing a beam trajectory along a scanning path TL, continuously emitted along the scanning path TL of the layer Ln in the case of continuous irradiation (line scanning or raster scanning) and emitted to a plurality of irradiation spots of the layer Ln in the case of spot scanning. The particle beam B is emitted along a scanning path TL1 extending in the X-axis direction, slightly shifted in the Y-axis direction along a scanning path TL2, and emitted along the adjacent scanning path TL1. In this manner, the particle beam B emitted from the irradiation unit 2 controlled by the control unit 7 moves on the scanning path TL.

Figure 4:
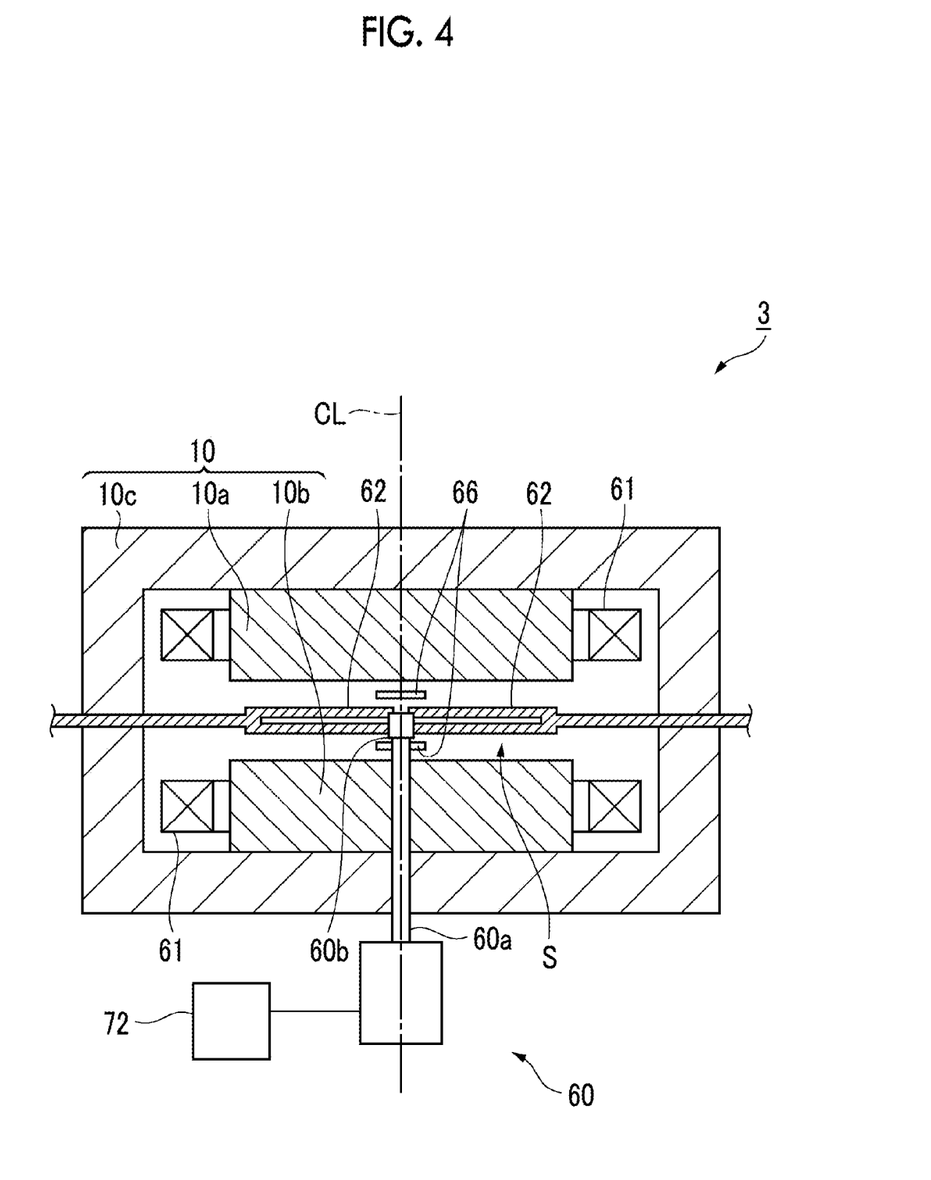
FIG. 4 is a schematic cross-sectional view of an accelerator according to the embodiment of the present invention.
Figure 5:
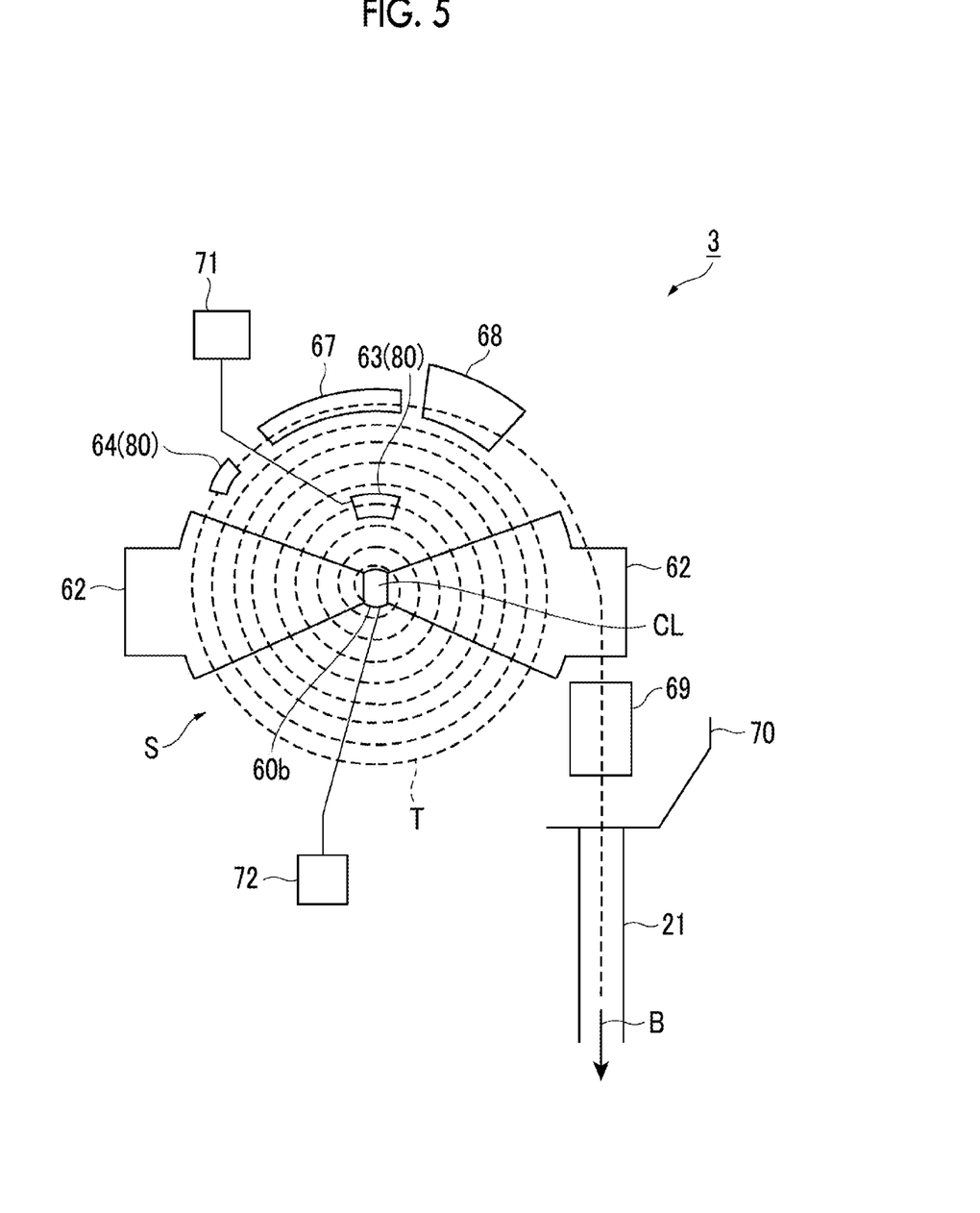
FIG. 5 is a schematic plan view of the accelerator according to the embodiment of the present invention.

The accelerator 3 will be described in more detail with reference to FIGS. 4 and 5. FIG. 4 is a schematic cross-sectional view of the accelerator 3. FIG. 5 is a schematic plan view of the accelerator 3. The accelerator 3 is a device that turns charged particles around a central axis CL to generate the particle beam B.

As illustrated in FIGS. 4 and 5, the accelerator 3 includes a core 10, an ion source device 60 (particle generation unit), coils 61, dee electrodes 62, a deflector 63, and a damper 64. The core 10 has an upper magnetic pole 10a and a lower magnetic pole 10b that face each other in the direction in which the central axis CL extends and form a main magnetic field and a yoke portion 10c that magnetically connects the magnetic poles 10a and 10b. The magnetic poles 10a and 10b are positioned in a vacuum box (not illustrated) that has a vacuumized inner portion.

The ion source device 60 generates charged particles such as ions. When the charged particles generated by the ion source device 60 reach the central portion of the accelerator 3 through a conduit 60a, the direction is bent from the up-down direction to the horizontal direction by an inflector 60b positioned in the tip portion of the conduit 60a. The on and off of the particle beam B can be switched by a pair of electrodes 66 (see FIG. 4). Next, the magnetic field formed by the core 10 and the coil 61 causes the particles to be accelerated (see FIG. 5) while turning while drawing a circular trajectory T (spiral trajectory directed outward from the central axis CL of the accelerator 3) along a predetermined trajectory plane MH (see FIG. 6). As a result, the particle beam B is generated. In other words, the region in the vacuum box and between the magnetic poles 10a and 10b functions as a charged particle acceleration space S (see FIG. 4). Subsequently, the circular trajectory T of the particle beam is finely adjusted by a deflector 67 and a magnetic channel 68 and converged by a quadrupole magnet 69 and the particle beam B emitted via a beam outlet 70 is introduced into the beam transport line 21 (see FIG. 5). The ion source device 60 may be disposed in the accelerator 3. In this case, the inflector 60b or the like is unnecessary. The ion source device 60 operates based on a parameter set by an ion source control unit 72.

As illustrated in FIG. 4, the coil 61 is used to form a main magnetic field. The coil 61 includes a first part disposed so as to surround the outer periphery of the upper magnetic pole 10a and a second part disposed so as to surround the outer periphery of the lower magnetic pole 10b. The first and second parts are electrically connected in series.

The dee electrode 62 is a fan-shaped electrode. The dee electrode 62 is disposed between the magnetic poles 10a and 10b, that is, in the acceleration space S. The dee electrodes 62 face each other in the direction in which the central axis CL extends so as to be positioned with a trajectory plane therebetween. The dee electrode 62 is connected to a high-frequency power supply (not illustrated). The high-frequency power supply supplies high-frequency electric power to the dee electrode 62 to generate an alternating current electric field (high-frequency electric field) in which the cycle of the electric field changes at regular intervals between the dee electrodes 62. Charged particles are accelerated each time the particles pass through the dee electrodes 62 by synchronizing the timing at which the particles pass between the dee electrodes 62 and the cycle of the high-frequency electric field.

The deflector 63 is provided at a position different from that of the dee electrode 62 in the circumferential direction. The damper 64 is disposed on the downstream side of the deflector 63 in the advancing direction of the particle beam B. The deflector 63 is configured by a pair of electrodes facing each other in the direction in which the central axis CL extends so as to sandwich a trajectory plane, and a power supply 71 applying a voltage to the pair of electrodes is connected to the deflector 63.

Figure 6:
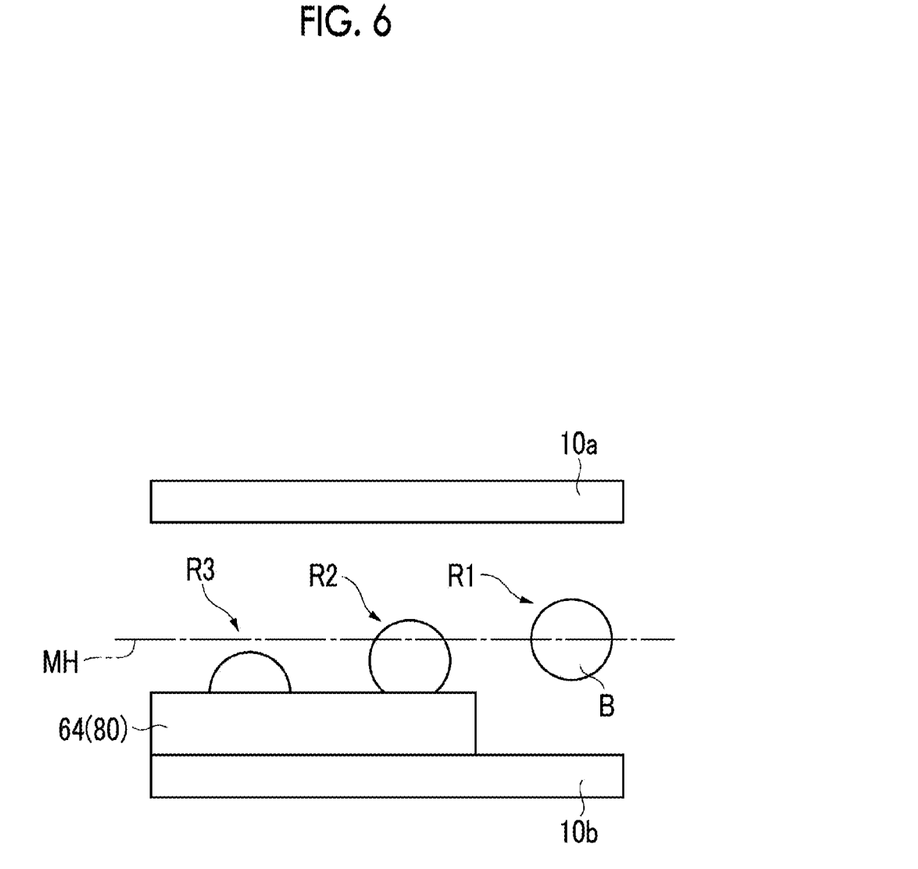
FIG. 6 is a schematic diagram illustrating how a part of a particle beam is scraped with a damper.

In the accelerator 3, as illustrated in FIG. 6, the particle beam B is bent upward from a circling position R1 to circling positions R2 and R3 by the deflector 63 (see FIG. 5) and is scraped by the damper 64. In this manner, the deflector 63 and the damper 64 function as an adjusting unit 80 adjusting the intensity of the particle beam B. The adjusting unit 80 adjusts the intensity of the particle beam B by bending the particle beam B with the deflector 63 and scraping a part of the particle beam B with the damper 64 in the acceleration space S.

Here, the accelerator 3 sets a parameter of the ion source device 60 based on at least one layer Ln of the tumor 14 and adjusts the intensity of the particle beam B based on the set parameter. In other words, the accelerator 3 adjusts the intensity of the particle beam B by setting a parameter of the ion source device 60 based on at least one layer Ln of the tumor 14 and controlling the amount of scraping of the particle beam B by the adjusting unit 80. In the present embodiment, the accelerator 3 sets the parameter of the ion source device 60 based on one layer Ln. In other words, the accelerator 3 sets the parameter of the ion source device 60 for each layer Ln.

Figure 7A:
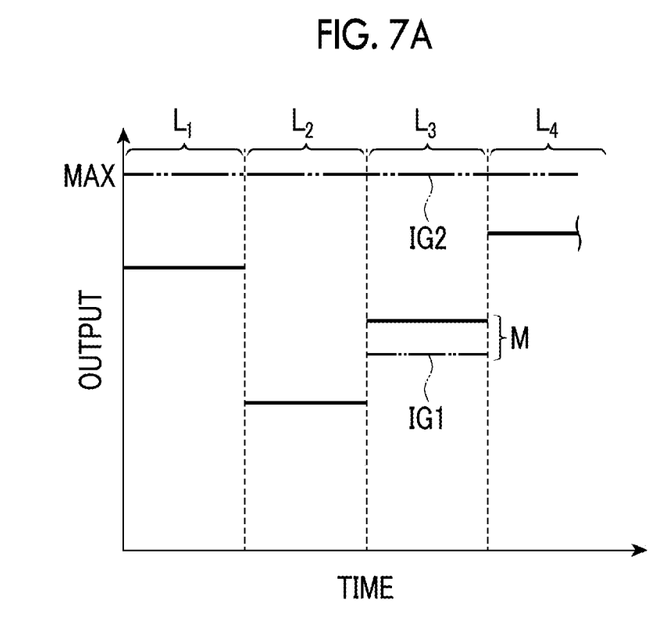
FIGS. 7A and 7B are graphs illustrating the intensity of the particle beam that can be output by particles generated by an ion source device.

The ion source control unit 72 sets a plasma parameter for each layer Ln. The plasma parameter is a parameter that determines plasma intensity when the ion source device 60 generates plasma for particle generation. Examples of the plasma parameter include bias current, bias voltage, and cathode temperature. As a result, the intensity of the particle beam B that can be output by the particles generated by the ion source device 60 is different for each layer Ln as illustrated in, for example, FIG. 7A.

The ion source control unit 72 sets the parameter of the ion source device 60 based on the maximum intensity for one layer Ln. For example, in the layer L3 of FIG. 7A, the maximum current value (maximum intensity) of the particle beam B in the layer is represented by "IG1". This maximum current value IG1 is the maximum value in one layer L3 and thus is lower than a maximum current value IG2 as the output of the accelerator 3.

The ion source control unit 72 sets the parameter of the ion source device 60 such that an output in which a predetermined current value is increased with respect to the maximum current value (maximum intensity) for one layer Ln can be obtained. For example, in the example of FIG. 7A, the ion source control unit 72 sets the plasma parameter such that an output in which an increase current value M is added to the maximum current value IG1 for one layer L3 can be obtained. Specifically, the ion source control unit 72 sets the plasma parameter such that the output is 10% higher than the maximum current value IG1. The increase current value M is not limited to 10% and may be set in the range of, for example, 5 to 100%.

The accelerator 3 controls the particle beam B output with the plasma parameter determined as described above for one layer Ln with the adjusting unit 80 to adjust the intensity of the particle beam B. The power supply 71 sets the initial value of the voltage (chopper voltage) of the deflector in the target layer Ln to a value corresponding to the current value to the first spot in the layer Ln. Then, the power supply 71 adjusts the chopper voltage such that the current value corresponds to the weight of each spot in the layer Ln such that the current value for the subsequent spots can be obtained. While the irradiation unit 2 irradiates the layer Ln with the particle beam B, the ion source control unit 72 keeps the plasma parameter constant. The power supply 71 changes the chopper voltage in accordance with the irradiation position in the layer Ln to adjust the amount of scraping of the particle beam B by the adjusting unit 80 and obtain the particle beam B of desired intensity. For example, in a case where the intensity of the particle beam B with respect to an irradiation position P2 is higher than the intensity of the particle beam B with respect to an irradiation position P1 in FIG. 3B, the power supply 71 increases the chopper voltage such that the amount of scraping of the particle beam B at the irradiation position P1 is larger than the amount of scraping of the particle beam B at the irradiation position P2.

Figure 8:
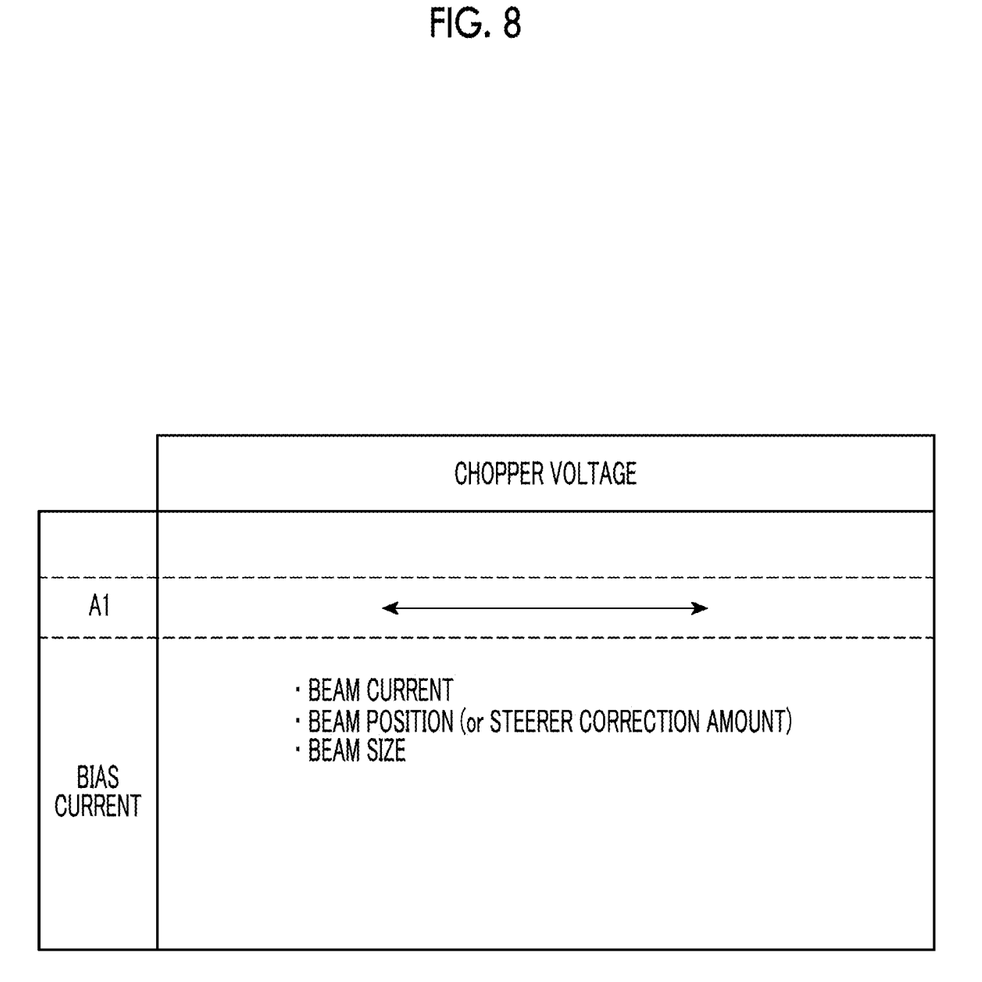
FIG. 8 is a diagram illustrating an image of a data table.

Here, the accelerator 3 controls the adjustment of the intensity of the particle beam B, that is, the amount of scraping of the adjusting unit 80 based on a data table prepared in advance. For example, a data table as illustrated in FIG. 8 is prepared in advance. In creating the data table, the cathode temperature of the ion source device 60 is set to a cathode temperature at which maximum current output is possible. Next, bias current setting to a predetermined value is performed without changing the cathode temperature and the irradiation unit 2 emits the particle beam B. At this time, the particle beam B is emitted while changing the chopper voltage of the power supply 71 and each parameter is measured. Examples of the parameters to be measured include "beam current", "beam position (or steerer correction amount)", and "beam size" of the particle beam B output from the accelerator 3. The beam current is the intensity of the output particle beam B. The beam position is the position (magnitude of deviation) of the particle beam B at the outlet of the accelerator. The position of the particle beam B can be measured with a beam monitor provided at the outlet of the accelerator. The steerer correction amount is the magnitude of the deviation correction amount at a time when the position is adjusted from the beam position. The beam size is the diameter of the output particle beam B.

Based on the result of the above measurement, it is possible to create a data table regarding the parameter of the particle beam B that can be obtained when a predetermined bias current and a predetermined chopper voltage are set. In the data table, the parameter of the particle beam B for the intermediate bias current between the set value of a certain bias current and the set value of the next bias current is complemented by calculation and interpolation. Likewise, the parameter of the particle beam B for the intermediate chopper voltage between the set value of a certain chopper voltage and the set value of the next chopper voltage is complemented by calculation and interpolation. Such a data table is stored in the storage unit 95 illustrated in FIG. 2. When the treatment planning device 90 creates a scanning pattern, the bias current in the ion source device 60 is set with reference to the maximum current value in each layer. In addition, the treatment planning device 90 grasps the parameter of the particle beam B to be irradiated at each irradiation position of each layer and determines the chopper voltage at each irradiation position in light of the data table. For example, in a case where the bias current of a certain layer is "A1", the treatment planning device 90 compares the parameter of the particle beam B in the "A1" row of the data table with the parameter at each irradiation position to determine a matching chopper voltage (see FIG. 8). As a result, the treatment planning device 90 is capable of determining a scanning pattern and the bias current and the chopper voltage corresponding to the scanning pattern. In emitting the particle beam B, the control unit 7 sends a command value to the power supply 71 and the ion source control unit 72 and sets the bias current and the chopper voltage at a timing corresponding to the created scanning pattern.

Even in a case where a scanning pattern is created in accordance with the data table as described above, the parameter of the particle beam B in actual irradiation may deviate from a plan. For example, the irradiation unit 2 is capable of grasping the deviation from a planned value by monitoring the current value (intensity) of the particle beam B with the dose monitor 12 (detection unit). In a case where the deviation is detected, the control unit 7 does not refer to the data table again to correct the chopper voltage but feeds back a detection result on the detected deviation to the power supply 71 to control the adjustment of the intensity of the particle beam B, that is, the amount of scraping of the particle beam B of the adjusting unit 80. In a case where the detected deviation exceeds a predetermined amount, the data table is recreated by the above measurement during maintenance or the like.

Figure 9:
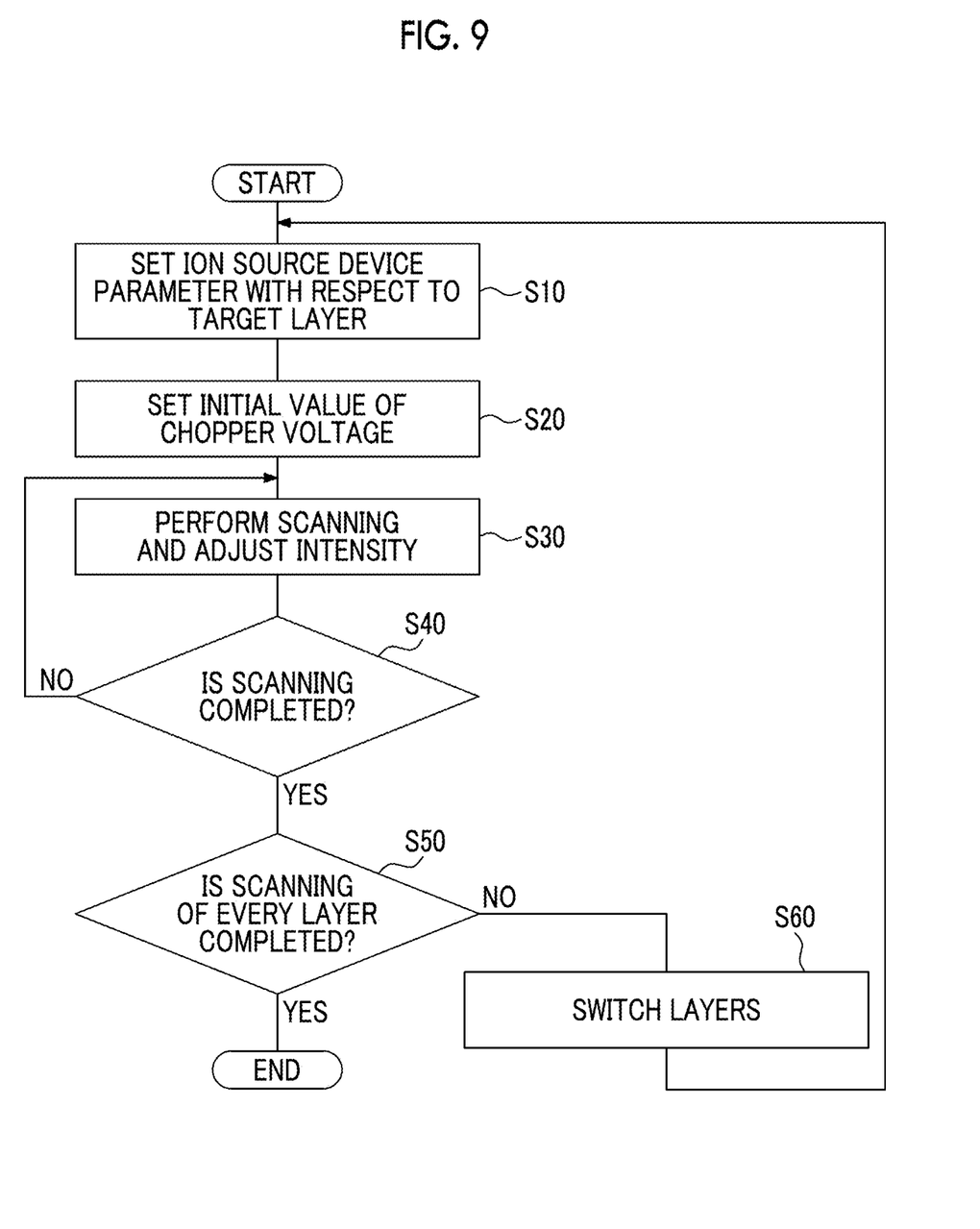
FIG. 9 is a flowchart illustrating the content of processing in the particle beam treatment apparatus.

Next, the processing content at a time when the irradiation unit 2 irradiates the tumor 14 with the particle beam B to perform treatment will be described with reference to FIG. 9. The processing is executed by the control unit 7. The control unit 7 acquires the data of the treatment planning created in advance by the treatment planning device 90 before performing the processing of FIG. 9. First, the control unit 7 sets the parameter of the ion source device 60 for the layer to be irradiated (Step S10). Next, the control unit 7 sets the initial value of the chopper voltage of the deflector 63 based on the current value (intensity) to the first spot of the target layer (Step S20). Then, the control unit 7 performs scanning while irradiating the target layer with the particle beam B and adjusts the amount of scraping of the particle beam B in the adjusting unit 80 to adjust the intensity at each irradiation position (Step S30). Next, the control unit 7 determines whether or not the target layer is completely scanned (Step S40). In the case of a non-completion determination, the control unit 7 repeats Step S30. In the case of a completion determination, the control unit 7 determines whether or not every layer is completely scanned (Step S50). In the case of a non-completion determination, the control unit 7 switches layers (Step S60) and repeats the processing from Step S10. The processing illustrated in FIG. 9 ends in a case where it is determined that every layer is completely scanned.

Next, the actions and effects of the particle beam treatment apparatus 1 and the accelerator 3 according to the present embodiment will be described.

In the particle beam treatment apparatus 1, the accelerator 3 includes the adjusting unit 80 adjusting the intensity of the particle beam B by bending the particle beam B with the deflector 63 and scraping a part of the particle beam B with the damper 64 in the acceleration space S. Accordingly, the adjusting unit 80 adjusts the amount of scraping such that the intensity corresponding to the irradiation position of the particle beam B can be obtained and thus is capable of obtaining a desired dose by short-time irradiation even without irradiating the irradiation position for a long time.

Figure 7B:
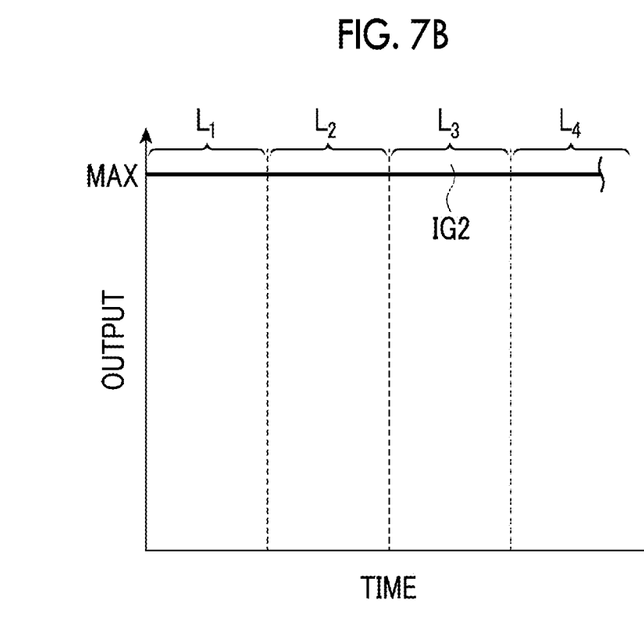

Here, the parameter of an ion source device of an accelerator according to a comparative example will be described with reference to FIG. 7B. In the comparative example, the parameter of the ion source device is set such that the maximum current value IG2 as the output of the accelerator can be output. As a result, the output of the particle beam B becomes the maximum current value IG2 for every layer. However, in the comparative example, the ion source device is operated such that the maximum current value IG2 can be obtained at all times, and thus there is a disadvantage that the maintenance cycle is shortened (for example, two weeks or so). In addition, even if the part where the intensity of the particle beam B is low is scraped with the damper 64, the particle beam B of high current value is scraped at all times, and thus there is a disadvantage that the surrounding structure is affected by spattering. In addition, the deflector 63 is required to bend the particle beam B of high intensity at all times, and thus high-accuracy intensity adjustment may be impossible depending on the output intensity unless the resolution of the set voltage of the power supply of the deflector 63 is satisfactory. In addition, the ion source device may become unstable.

On the other hand, in the present embodiment, the accelerator 3 sets the parameter of the ion source device 60 based on at least one layer of the tumor 14 and adjusts the intensity of the particle beam B by controlling the amount of scraping of the particle beam B by the adjusting unit 80. In a case where the maximum intensity of the particle beam B required in the layer to be irradiated is low in this case, the ion source device 60 is capable of generating particles in a state of being suppressed to a parameter capable of corresponding to a low intensity (see, for example, the layers L2 and L3 in FIG. 7A). As a result, the parameter at the ion source device 60 can be suppressed to an appropriate size. In addition, the accelerator 3 adjusts the intensity of the particle beam B such that a dose corresponding to the irradiation position of the particle beam B can be obtained, and thus a desired dose can be obtained by short-time irradiation even without irradiating the irradiation position for a long time. From the above, it is possible to increase the scanning speed of the particle beam B while adjusting the intensity of the particle beam B in an appropriate adjustment mode.

The accelerator 3 may set the parameter of the ion source device 60 based on the maximum intensity for at least one layer. The adjusting unit 80 adjusts the intensity by scraping a part of the particle beam B with the damper 64, and thus it is impossible to perform the adjustment by increasing the intensity. Accordingly, it is possible to suppress an insufficient intensity of the output particle beam by setting the parameter of the ion source device 60 based on the maximum intensity with respect to the layer.

The accelerator 3 may set the parameter of the ion source device 60 so as to obtain an output in which a predetermined intensity is increased with respect to the maximum intensity. In this case, it is possible to suppress an insufficient intensity by increasing the intensity in advance even in a case where the intensity of the particle beam B that is scraped with the damper becomes lower than planned due to the output of the particle beam B becoming unstable.

The accelerator 3 may adjust the intensity of the particle beam B based on the data table prepared in advance. In this case, the accelerator 3 is capable of appropriately adjusting the amount of scraping of the adjusting unit 80 with the load of calculation reduced.

The irradiation unit 2 has the dose monitor 12 (detection unit) that detects the intensity of the particle beam B, and the accelerator 3 may feed back the detection result of the dose monitor 12 to adjust the intensity of the particle beam B. In this case, the amount of scraping of the adjusting unit 80 can be appropriately controlled based on the detection result at the dose monitor 12 even in a case where the intensity of the particle beam B is different from a planned one.

The accelerator 3 according to one aspect of the present embodiment virtually divides an irradiation target into a plurality of layers and generates the particle beam B for irradiating each layer by a scanning method. The accelerator 3 according to one aspect of the present embodiment includes the ion source device 60 that generates particles in an acceleration space, sets the parameter of the ion source device 60 based on at least one layer of the irradiation target, and adjusts the intensity of the particle beam B based on the set parameter.

According to this accelerator 3, it is possible to obtain the same action and effect as the particle beam treatment apparatus 1 described above.

The present invention is not limited to the embodiment described above.

For example, the parameter of the ion source device may not be set for each layer and one parameter may be collectively set for a plurality of layers.

Although a cyclotron has been exemplified as an accelerator in FIGS. 4 and 5, the configuration of the present invention may be adopted for various accelerators such as a synchrocyclotron and a linear accelerator (linac).

It should be understood that the invention is not limited to the above-described embodiment, but may be modified into various forms on the basis of the spirit of the invention. Additionally, the modifications are included in the scope of the invention.

What is claimed is:

1. A particle beam treatment apparatus irradiating an irradiation target with a particle beam, the apparatus comprising:
    an accelerator that generates the particle beam in an acceleration space; and
    an irradiation unit that virtually divides the irradiation target into a plurality of layers and irradiates each layer while performing scanning with the particle beam with a scanning electromagnet,
    wherein the accelerator includes a particle generation unit generating particles that are to accelerate in the acceleration space,
    the accelerator sets a parameter of the particle generation unit based on at least one of the layers of the irradiation target and adjusts an intensity of the particle beam based on the set parameter, and
    the accelerator includes an adjusting unit adjusting the intensity of the particle beam by bending the particle beam with a deflector and scraping a part of the particle beam with a damper in the acceleration space.

2. The particle beam treatment apparatus according to claim 1,
    wherein the accelerator sets the parameter of the particle generation unit based on a maximum intensity for at least one of the layers.

3. The particle beam treatment apparatus according to claim 2,
    wherein the accelerator sets the parameter of the particle generation unit so as to obtain an output in which a predetermined intensity is increased with respect to the maximum intensity.

4. The particle beam treatment apparatus according to claim 3,
    wherein the accelerator sets the parameter of the particle generation unit for an output high in a range of 5 to 100% with respect to the maximum intensity.

5. The particle beam treatment apparatus according to claim 1,
    wherein the accelerator adjusts the intensity of the particle beam based on a data table prepared in advance.

6. The particle beam treatment apparatus according to claim 1,
    wherein the irradiation unit has a detection unit detecting the intensity of the particle beam, and
    the accelerator feeds back a detection result of the detection unit to adjust the intensity of the particle beam.

7. The particle beam treatment apparatus according to claim 1,
    wherein the irradiation unit has an irradiation nozzle, and the irradiation nozzle accommodates a scanning electromagnet, a quadrupole electromagnet, a profile monitor, a detection unit, a position monitor, a collimator, and a degrader.

8. The particle beam treatment apparatus according to claim 7,
wherein the scanning electromagnet is configured by a pair of an X-axis direction scanning electromagnet and a Y-axis direction scanning electromagnet, and
the scanning electromagnet is disposed on a downstream side of the particle beam from the accelerator.

9. The particle beam treatment apparatus according to claim 7,
wherein the quadrupole electromagnet is configured by an X-axis direction quadrupole electromagnet and a Y-axis direction quadrupole electromagnet, and
the quadrupole electromagnet is disposed between the accelerator and the scanning electromagnet.

10. The particle beam treatment apparatus according to claim 7,
wherein the profile monitor is disposed between the quadrupole electromagnet and the scanning electromagnet and detects a beam shape and a position of the particle beam, and
the position monitor is disposed on a downstream side of the particle beam from the detection unit and detects and monitors the beam shape and the position of the particle beam.

11. The particle beam treatment apparatus according to claim 7,
wherein the collimator is provided on a downstream side of the particle beam from the scanning electromagnet and is a member blocking the particle beam in part and allowing the particle beam to pass in part.

12. The particle beam treatment apparatus according to claim 7,
wherein the degrader is provided in a tip portion of the irradiation nozzle to adjust the intensity of the particle beam.

13. The particle beam treatment apparatus according to claim 1, further comprising:
a beam transport line transporting the particle beam emitted from the accelerator to the irradiation unit.

14. An accelerator that virtually divides an irradiation target into a plurality of layers and generates a particle beam for irradiating each layer by a scanning method, the accelerator comprising:
a particle generation unit generating particles in an acceleration space; and
an adjusting unit adjusting an intensity of the particle beam by bending the particle beam with a deflector and scraping a part of the particle beam with a damper in the acceleration space,
wherein a parameter of the particle generation unit based on at least one of the layers of the irradiation target is set and the intensity of the particle beam is adjusted based on the set parameter.

* * * * *